(12) United States Patent
Alkhalaf (10) Patent No.: US 9,470,519 B2
(45) Date of Patent: Oct. 18, 2016

(54) APPARATUS FOR DETERMINING A DIMENSION OF A SELECTED SURFACE OF AN OBJECT

(71) Applicant: King Saud University, Riyadh (SA)

(72) Inventor: Rakan Khaled Y. Alkhalaf, Riyadh (SA)

(73) Assignee: King Saud University, Rihadh (SA)

( * ) Notice: Subject to any disclaimer, the term of this patent is extended or adjusted under 35 U.S.C. 154(b) by 212 days.

(21) Appl. No.: 14/351,073

(22) PCT Filed: Dec. 7, 2012

(86) PCT No.: PCT/IB2012/002642
§ 371 (c)(1),
(2) Date: Apr. 10, 2014

(87) PCT Pub. No.: WO2013/054202
PCT Pub. Date: Apr. 18, 2013

(65) Prior Publication Data
US 2014/0298667 A1    Oct. 9, 2014

(30) Foreign Application Priority Data
Oct. 11, 2011    (EP) .................................... 11184616

(51) Int. Cl.
*G01B 21/00*    (2006.01)
*G01B 21/20*    (2006.01)
*A61B 5/107*    (2006.01)
*A41H 1/02*    (2006.01)
*A61B 5/00*    (2006.01)

(52) U.S. Cl.
CPC ............... *G01B 21/20* (2013.01); *A61B 5/107* (2013.01); *A61B 5/1077* (2013.01); *A41H 1/02* (2013.01); *A61B 5/1075* (2013.01); *A61B 5/6805* (2013.01); *A61B 2562/046* (2013.01)

(58) Field of Classification Search
CPC .............. G01B 2003/1069; G01B 2003/1094; G01B 3/1061; G01B 3/1082; G01B 3/1084; G01B 5/207; G01B 2210/28; G01B 3/12
USPC ........................................................... 33/512
See application file for complete search history.

(56) References Cited

U.S. PATENT DOCUMENTS 3,979,831 A    9/1976    Lutz
4,586,150 A    4/1986    Budziak
(Continued)

FOREIGN PATENT DOCUMENTS

| DE | 4008282 | 9/1991 |
|---|---|---|
| EP | 2581701 | 4/2013 |
| JP | 7035535 | 2/1995 |

OTHER PUBLICATIONS

PCT/IB2012/002642 filed Jul. 12, 2012, International Search Report dtd Feb. 20, 2013, 4pgs.

*Primary Examiner* — Yaritza Guadalupe-McCall
(74) *Attorney, Agent, or Firm* — Spencer Fane LLP (57) ABSTRACT

There is provided an apparatus configured to be used with a processing unit for determining a dimension of a selected surface of an object, the apparatus comprising i) a piece of stretchable fabric having a shape adapted to fit the selected surface of the object such that the piece of fabric stretches proportionally to the dimension of the surface when draped thereover; ii) a plurality of uniquely identified beacon devices disposed on the piece of fabric when unstretched in accordance with a first spatial configuration known a priori, where, when the piece of fabric is draped over and stretched by the surface, the beacon devices automatically shift position and form a second spatial configuration as a function of the dimension of the surface; and ii) electronic means for detecting the second spatial configuration and for generating data representing the second spatial configuration; where the processing unit is configured to receive data associated with the first and second spatial configurations and to determine the dimension of the surface as a function thereof.

38 Claims, 5 Drawing Sheets

(56) References Cited

U.S. PATENT DOCUMENTS

| | | | |
|---|---|---|---|
| 4,635,367 A | 1/1987 | Vigede | |
| 4,868,990 A * | 9/1989 | Steinberg | A41H 1/10 33/15 |
| 4,885,844 A * | 12/1989 | Chun | A41H 1/02 33/15 |
| 5,691,923 A | 11/1997 | Adler | |
| 5,956,525 A * | 9/1999 | Minsky | A41H 1/02 33/15 |
| 6,415,199 B1 * | 7/2002 | Liebermann | A41H 1/02 33/512 |
| 7,253,766 B2 | 8/2007 | Foote | |
| 7,484,408 B2 * | 2/2009 | Healey | G01F 17/00 33/1 V |
| 2003/0036858 A1 | 2/2003 | Friedrichs | |
| 2006/0140463 A1 | 6/2006 | Rutschmann | |
| 2010/0275338 A1 * | 11/2010 | Hyde | A61B 5/1077 2/69 |
| 2013/0192071 A1 * | 8/2013 | Esposito | A61B 5/1036 33/6 |
| 2014/0298667 A1 * | 10/2014 | Alkhalaf | A61B 5/1077 33/514.2 |
| 2015/0342266 A1 * | 12/2015 | Cooper | A41B 11/00 33/2 R |

\* cited by examiner

APPARATUS FOR DETERMINING A DIMENSION OF A SELECTED SURFACE OF AN OBJECT

FIELD OF THE INVENTION

The present invention generally relates to electronic measuring systems and apparatuses for electronically measuring physical dimensions of an object and, more particularly to an apparatus configured to be used with a processing unit for determining a dimension of a selected surface of an object. In particular, the object may be a 3D-object and the selected surface may be a 3D-surface.

BACKGROUND OF THE INVENTION

Systems, apparatuses and methods of measuring physical dimensions of a body are useful in a variety of applications, among others, for taking a person's body measurements for garment tailoring purposes.

Traditional systems, apparatuses and methods of measuring physical dimensions of a body for tailoring purposes generally use manual measuring means, such as a measuring tape. The steps taken in tailoring a suit are familiar to anyone who has purchased a piece of cloth. The customer chooses a piece of cloth and then seeks assistance for taking a number of body measurements in order to alter the suit to fit the size of the customer. Sometimes the customer is fortunate enough to have the tailor take the measurements. The tailor will know if special considerations are required for the shape of the customer or the style of the suit. If this is the case, certain additional measurements may be necessary over and above the half dozen or so measurements normally taken. If, as an example, the customer has an athletic build with well developed thigh and bicep muscles, yet normal waist and shoulder measurements, additional measurements may be required to enable the tailor to produce a well fitting suit. It is also possible for the well-trained tailor to spot specifics in posture which may require additional measurements to be taken to more precisely match the suit to the customer.

In many retail stores, however, a tailor is not present at the store and the measurements are rather taken by a store clerk who may not know which measurements are needed for a particular individual. The tailor operates at a distinct disadvantage when alterations are made since he will undoubtedly tailor the suit to the universal build and posture rather than what may be a very uniquely proportioned person. In these instances, the clerk's measurements may result in only an average fit. Besides, the measurements taken by the store clerk should usually be sent manually to the tailor who is usually located in another location. This process of taking measurements is time consuming and usually results in inaccurate measurement results and defective tailored garments.

Recent developments in the field of data processing and electronics resulted in developing special technologies for electronically measuring physical dimensions of a human's body. Noticeable examples of the prior art are U.S. Pat. No. 7,253,766, to Foote et Al. (2007), U.S. Pat. No. 6,415,199, to Liebermann (2002), U.S. Pat. No. 4,885,844, to Chun (1989), U.S. Pat. No. 4,868,990, to Steinberg (1989), U.S. Pat. No. 4,635,367, to Vigede (1987), and U.S. Pat. No. 3,979,831, to Lutz (1976). Other examples of prior art are U.S. Pat. No. 4,635,367, U.S. Pat. No. 4,586,150, U.S. Pat. No. 5,691,923, U.S. Pat. No. 5,956,525.

US patent '367 suggests use of electrical connectors connected to a plurality of measuring points distributed over a body suit, where the electrical connectors detect emplacement of said measuring points when the body suit is worn by a person and transmit electrical signals representing said emplacements to be stored in storage means. This technology also suggests, as an alternative, optical sensors for detecting these measuring points. The measuring points are disposed on a tape that should be manually adjusted (by the tailor) according to the wearer's size.

US patent '150 teaches a hand held device for taking measurements. The device measures a distance between two points by extending a wire therebetween and by measuring the equivalent voltage of the wire. Since the voltage is proportional to the length of the wire, the distance between the two points is therefore determined. The measurements are sent by a transmitter to a receiver in order to be stored for potential use.

US patent '923 suggests a beacon device using a measuring tape having regularly-spaced markers and electronic sensing means for detecting passage of the markers. Once, the maker is detected, the measured distance is converted into an electrical signal and transmitted to be recorded.

US patent '525 suggests use of a multi-view camera arrangement for building a three dimensional profile of a person.

While these traditional measuring systems, apparatuses and methods may provide means for measuring physical dimensions of a person, these technologies require a human intervention in order to carry out at least some operations. Moreover, these technologies are complex, high costly and unreliable in certain circumstances. In fact, they generally do not provide substantially accurate measurement of the physical dimensions of a body, are complex and expensive to produce and generally require specialized training of persons using these systems and apparatuses. Besides, some of the associated equipments required to execute the measurements are generally cumbersome and, thus, are not in a compact format for facilitating the measurement process. Another limitation of these traditional systems and apparatuses is that, in being voluminous, they are unsuitable for shipping through regular post mail. Such a constraint is particularly disadvantageous in a growing global market environment and purchases of garments made by private individuals through Internet.

SUMMARY OF THE INVENTION

It is a general object of the present invention to provide a new and improved apparatus that overcome the above-mentioned drawbacks.

As a first aspect of the invention, there is provided An apparatus configured to be used with a processing unit for determining a dimension of a selected surface of an object, said apparatus comprising:
a measuring garment having a shape adapted to fit said selected surface of said object such that said piece of fabric stretches, in particular proportionally, to said dimension of said surface when draped thereover;
a plurality of uniquely identified beacon devices disposed on said measuring garment when unstretched in accordance with a first spatial configuration known a priori, where, when said measuring garment is draped over and stretched by said surface, at least one of said beacon devices automatically shifts position and forms a second spatial configuration as a function of said dimension of said surface; and electronic means for detecting said second spatial configuration and for generating data representing said second spatial configuration;

where said processing unit is configured to receive data associated with said first and second spatial configurations and to determine said dimension of said surface as a function thereof.

The beacon devices can be considered as markers or references of the system to be able to determine the shape and measurements of the dimensions.

A spatial configuration can be seen as a map defining where each beacon device of the beacon devices is located within the surface of the object. This generally requires an indication of the exact location (distance and orientation) of each beacon device with respect to the other beacon devices.

Preferably, the processing unit is part of a remote computer system, the apparatus further comprising communication means adapted to be connected to a data network for remotely transmitting the data representing the second spatial configuration to the processing unit.

Preferably, the electronic means comprise distance measuring means and/or the distance measuring means allow for determining a shifting length and a shifting orientation of each one of the beacon devices when the beacon devices shift position.

As will be illustrated hereinafter, in order to determine the shifting orientation, generally it is not required to have other means beside the distance measuring means. In most cases, the shifting orientation of a given beacon device can be determined by comparing the relative shifting length of the given beacon device with respect to its adjacent beacon devices. For instance, if a given beacon device (A) has four adjacent beacon devices (B, C, D and E) which are respectively located at 0, 90, 180 and 270 degrees from the given beacon device, by measuring the shifting length of the given beacon device with respect to each one of these adjacent beacon devices, the shifting orientation can be determined, and hence no other measuring means beside the distance measuring means are required.

Preferably, the distance measuring means comprise uniquely identified rotary encoders disposed within at least a part of the uniquely identified beacon devices in accordance with a rotary encoder configuration known a priori, wherein the rotary encoders comprise input rotatable shafts coupled to spring loaded reels storing strings, where the strings have a first end folded within the spring loaded reels and a second end extending therefrom and attached to attachment points located at selected directions in accordance with the rotary encoder configuration, such that when the beacon devices shift position, the strings unfold and engage the input rotatable shafts to rotate proportionally to the shifting.

Preferably, the strings are non-stretchable strings and the rotary encoders are configured to output rotational values proportional to the shifting when the input rotatable shafts rotate, where the shifting length and shifting orientation of each one of the beacon devices is determined as a function of the rotary encoder configuration and the rotational values.

In other terms, the rotary encoders are disposed in accordance with a rotary encoder configuration which is determined a priori and known a priori by the processing unit. The rotary encoder configuration can be seen as a map defining where each rotary encoder is located within the surface of the object to measure and where (distance and orientation) it's corresponding attach point is located with respect thereto. Each rotary encoder is uniquely identifier by a unique rotary identifier such that each rotational value can be associated with a given rotary encoder. Besides, the strings should be non-stretchable strings for enabling the input rotatable shafts to rotate proportionally to the tension exercised on the fabric. Otherwise (if the strings where stretchable), this tension would be at least partially dissipated by stretching the strings and the rotation of the rotary encoders would not be proportional to the exercised tension.

Preferably, the apparatus further comprises a central communication unit and communication means connected to the beacon devices and to the central communication unit, where the central communication unit receives the rotational values from the beacon devices, maps each rotational value among the rotational values with a corresponding rotary encoder among the rotary encoders by which it was generated, and remotely transmits the mapped rotational values to the processing unit.

The central communication unit can be connected directly to each rotary encoder for receiving the rotational values. Since the rotary encoders are uniquely identified, the central communication unit receives the rotational values and maps each read rotational value to the unique identifier of the rotary encoder by which it was generated. In other terms, the central communication unit generates a data matrix storing the rotational values in association with their respective unique rotary identifiers. A mapped rotational value is essentially a vector comprising a rotational value and its corresponding unique rotary identifier.

Preferably, the processing unit is part of a remote computer system, the central communication unit further comprising a network interface adapted to be connected to a data network for remotely transmitting the mapped rotational values to the processing unit. It should be understood that the data network can comprise more than one data network. For instance, it can comprise a Wi-Fi data network for transmitting the data to an intermediary computer system and of the Internet for transmitting the data from the intermediary computer system to the processing unit that can be located within a remote computer system with respect to the intermediary computer system and connected to the Internet.

Preferably, the beacon devices comprise storage means for storing the rotational values, wherein the communication means are connected to the storage means for retrieving the rotational values. It should be understood that the stored rotational values should be stored in such a manner that the central communication unit can associate each rotational value with a unique rotary identifier.

Preferably, the beacon devices are disposed on the piece of fabric in a two dimensional array configuration such that each beacon device has a number of adjacent beacon devices located at different directions thereof. It should be understood that a two dimensional array configuration would allow measuring a surface in opposition to a one dimensional array that only allows for measuring a length. The attach points can consist of dump beacon devices selected among the beacon devices. It should be understood that dump beacon devices are meant to be non-intelligent beacon devices that are essentially used as attach points. Generally, they do not comprise rotary encoders nor are they connected to the distance measuring means and to the central communication unit.

Preferably, each one of the beacon devices comprises a number of rotary encoders equivalent to the number of adjacent beacon devices such that each pair of rotary encoders located within adjacent beacon devices are linked therebetween by a common string extending from their respective spring loaded reels.

As mentioned hereinabove, in order to determine the second spatial configuration of the beacon devices (when the fabric is draped over the surface of the object and is stretched), rotary encoders can be used which would allow measuring rotational values thereof which are proportional to the shifting amount of the beacon devices. However, there are other means for determining the second spatial configuration of the beacon devices. In fact, what is important is to measure the shifting (distance and orientation) of the beacon devices with respect to their first spatial configuration. Since the original distances and orientations between the beacon devices (when the fabric is not stretched) are know a priori, the objective is to determine the relative distances and orientations between the beacon devices after that fabric is draped over the surface of the object and is stretched. A person skilled in the art should understand that the means for measuring these relative positions can vary.

In another preferred embodiment, the distance measuring means comprise uniquely identified wire loaded reels disposed within at least a part of the uniquely identified beacon devices in accordance with a reel configuration known a priori, wherein the wire loaded reels store electrical wires having a first end folded within the wire loaded reels and a second end extending therefrom and attached to attach points located at selected directions in accordance with the reel configuration, such that when the beacon devices shift position, the electrical wires unfold and extend in length proportionally to the shifting.

Preferably, the distance measuring means further comprise electrical means for measuring electrical properties of the wires when unfolded by effect of the shifting, the electrical properties varying as a function of lengths of the wires, where the shifting length and shifting orientation of each one of the beacon devices is determined as a function of the reel configuration and the measured electrical properties. Preferably, the electrical properties consist, of electrical resistances or conductances of the wires.

Preferably, the apparatus further comprises a central communication unit and communication means connected to the beacon devices and to the central communication unit, where the central communication unit receives the measured electrical properties from the beacon devices, maps each measured electrical property among the measured electrical properties with a corresponding wire reel among the wire reels associated therewith, and remotely transmits the mapped measured electrical properties to the processing unit.

Preferably, the processing unit is part of a remote computer system, the central communication unit further comprising a network interface adapted to be connected to a data network for remotely transmitting the mapped measured electrical properties to the processing unit. Preferably, the beacon devices comprise storage means for storing the measured electrical properties, wherein the communication means are connected to the storage means for retrieving the measured electrical properties.

Preferably, the beacon devices are disposed on the piece of fabric in a two dimensional array configuration such that each beacon device has a number of adjacent beacon devices located at different directions thereof. The attach points can consist of dump beacon devices selected among the beacon devices.

Preferably, each one of the beacon devices comprises a number of wire loaded reels equivalent to the number of adjacent beacon devices such that each pair of wire loaded reels located within adjacent beacon devices are linked therebetween by a common electrical wire extending from their respective wire loaded reels.

Preferably, the object to measure is a part of a human body and the piece of fabric is a garment.

Other advantages and novel features of the present invention will be more apparent from the following drawings and detailed description.

DETAILED DESCRIPTION OF THE INVENTION

Figure 1:
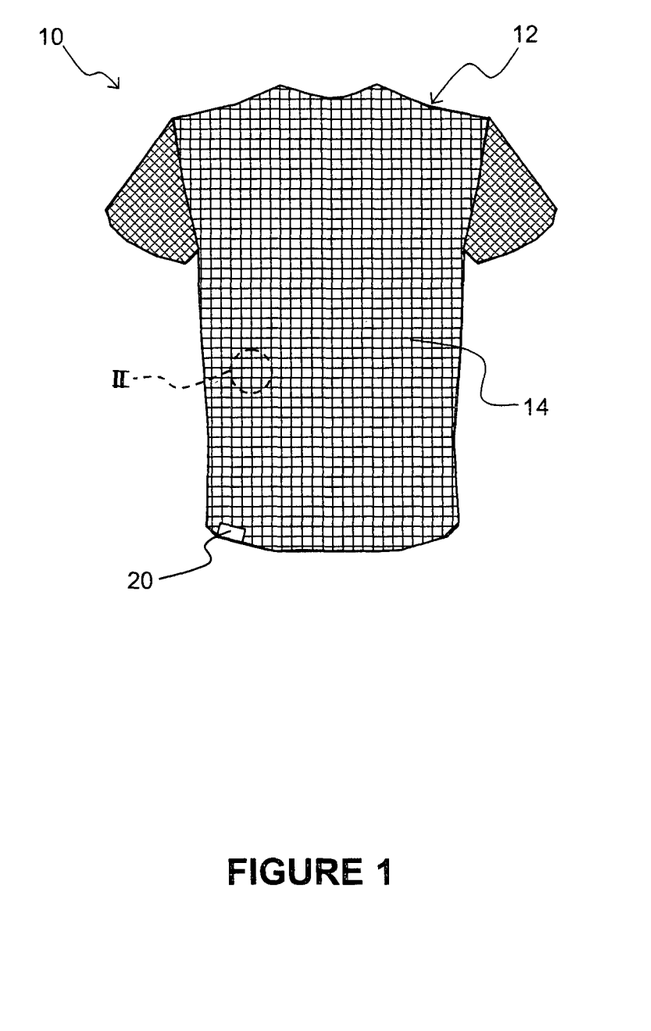
FIG. 1 shows a general view of an apparatus comprising a garment for measuring the upper part of a person's dimension in accordance with an embodiment of the present invention.

FIG. 1 illustrates an electronic measuring apparatus 10 according to a preferred embodiment of the present invention. The electronic measuring apparatus 10 comprises a body suit 12, a plurality of beacon devices 16 (see FIG. 2) and a central communication device 20. The present apparatus will be illustrated for measuring physical dimensions of a person, however it shall be understood that the present apparatus can be used to measure any object. In the present, an "object" is referred to be anything that is tangible and can be a person, an animal or a thing or any physical part thereof.

Though the body suit 12 is herein represented by a conventional T-shirt, it is to be understood that the body suit 12 may be represented by any other suitable piece of garment such as a long sleeve shirt, a pair of long pants, a pair of short pants, socks, gloves, a bonnet style head cover and a full body suit. In fact, the form of the body suit 12 shall be suited with the form of the object whose dimensions are to be measured. For example, if the objective is to measure a leg of a person, the body suit 12 shall comprise a piece of garment suitably fabricated to fit a leg of a human being. On the other hand, if the objective is to measure the physical dimensions of an animal body (ex. a dog), the body suit 12 shall comprise a piece of garment appropriately conceived to take the form of that animal.

The body suit 12 is made of a stretchable material, where the material has a non-stretched state when the body suit 12 is unworn (i.e. initial state), and is stretched by a given stretched amount when the body suit is worn (i.e. final state). The body suit 12 is preferably dimensioned such that it is slightly smaller than the regular clothing size of the wearer. Thus, once the body suit 12 is worn, it is stretched and closely conforms to the body portion of the wearer that it is designed to cover. Preferably, the stretchable property of the body suit 12 is such that a same size of the body suit 12 may be suitable to comfortably and closely conform to the body of wearer's who normally wear substantially different sizes of clothing. Thus, a relatively small number of a body suits 12 (ex. small, medium, large and extra-large sizes) may be sufficient to measure the body dimensions of a fairly large proportion of the population.

The electronic measuring apparatus 10 comprises a plurality of beacon devices 16 spatially distributed within the body suit 12. The beacon devices 16 are spatially arranged in an appropriate configuration, such as a substantially array configuration, a partial array configuration or a daisy-chained configuration. Each beacon device 16 is uniquely identified and is located at a pre-determined specific location of the body suit 12. Moreover, at an initial state (where the body suit is in a non-stretched state), the beacon devices are physically distant with respect to each other by a pre-determined and a priori known distance (initial distance). The specific configuration of the beacon devices at this initial state is referred to as "a first spatial configuration".

When the body suit is worn by a person, the body suit is stretched, and thus the beacon devices shift position with respect to each other and the distance therebetween increases (final distance). By measuring the final distance between the beacon devices 16, it is possible to determine the difference between the initial distance and the final distance therebetween (delta distance). In order to measure the final distance, each beacon device 16 is configured to obtain various measurement values of distance (and orientation) with respect to adjacent beacon devices 16. In a preferred embodiment, these measurement values are time stamped. This final disposition of the beacon devices (after the body suit is stretched) is referred to as "a second spatial configuration".

It should be understood that when it is referred to the distance between the beacon devices, it is meant to refer to a set of distance values that can be represented by a data matrix, where each value thereof represents a distance between two beacon devices. Thus, the initial distance, the final distance and the delta distance can be represented by data matrices comprising a set of distance values, where each value represents a distance between two adjacent beacon devices. These values would allow for determining the second spatial configuration. The first and second spatial configurations would allow for determining the physical dimensions of the wearer wearing the body suit 12.

Figure 3:
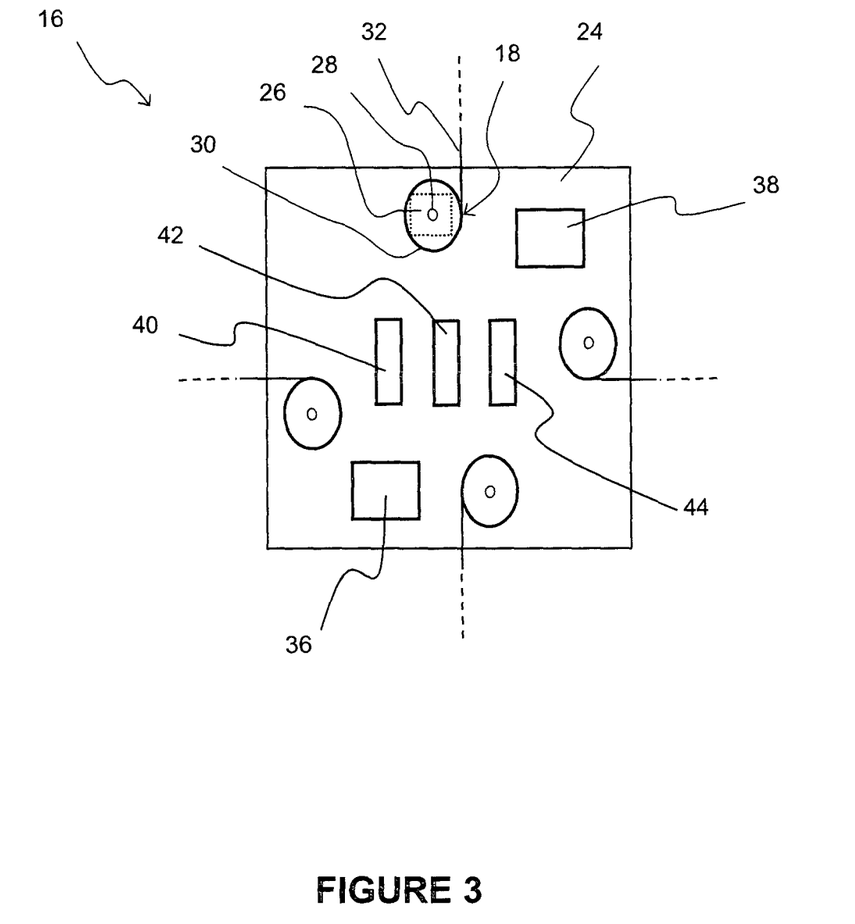
FIG. 3 depicts an enlarged view of a beacon device.

Now referring more particularly to FIG. 3, each beacon device 16 comprises distance measuring means 18 for measuring the various distances between said beacon device and adjacent beacon devices, storage means 42 for storing the obtained measured distance values, communication means 44 for transmitting the measured distance values (and other measured values if it is the case) to a central communication unit 20, and a support 24 on which the various components of the beacon device 16 stand.

Figure 2:
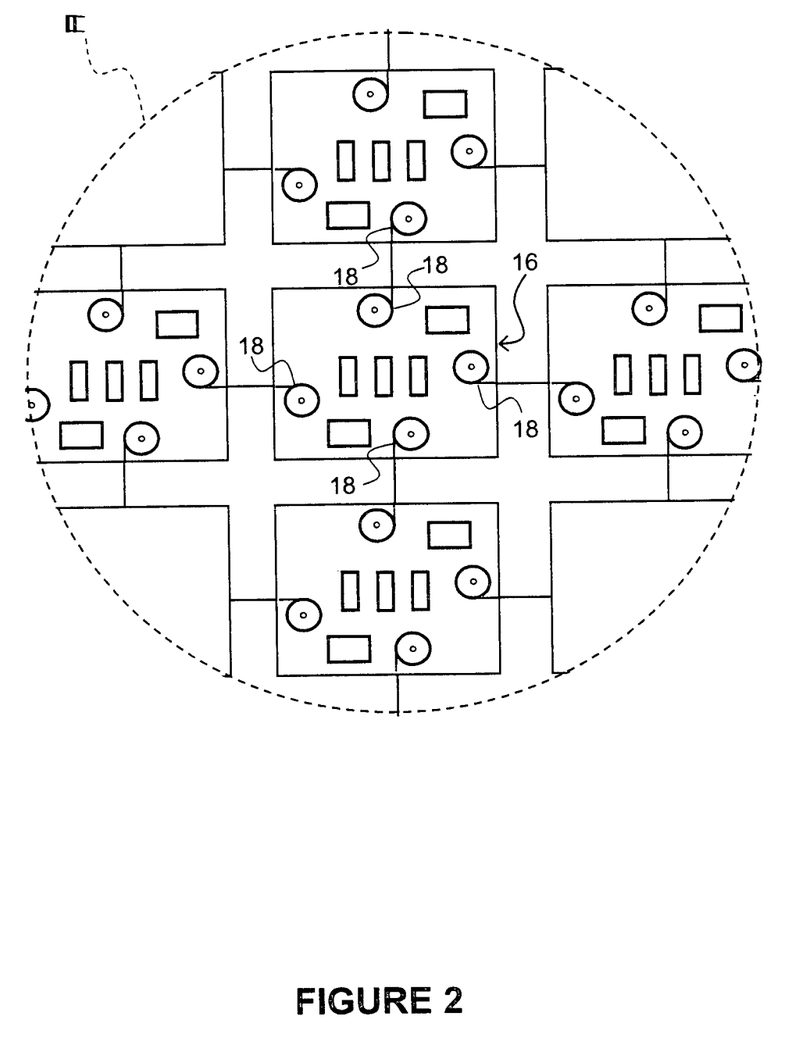
FIG. 2 depicts in an enlarged partial view of the section II of FIG. 1, wherein adjacent beacon devices are shown with a top portion removed for a better view of their internal structure.

FIG. 2 shows a particular array configuration of the beacon devices 16 according to a preferred embodiment. Accordingly, the beacon devices 16 have a square shape and are arranged in a matrix form configuration such as each beacon device has four adjacent beacon devices. The distance measuring means 18 can be configured such that the various distances between a given beacon device and adjacent beacon devices are measured. It should be understood that according to a preferred embodiment, the distance measuring means 18 allow for measuring the distances between a given beacon device and four adjacent beacon devices, however a person skilled in the art shall understand that it is possible to measure the distances between a given beacon device and a superior or an inferior number of adjacent beacon devices, which would respectively increase or decrease the resolution (precision) of the measuring apparatus 10. In other terms, the resolution of the measuring apparatus 10 can be increased or decreased by engaging an appropriate number and configuration of beacon devices 16 such that the number of adjacent beacon devices is respectively increased or decreased.

According to the preferred embodiment, the distance measuring means 18 are preferably distributed about a circumferential edge of each beacon device 16. The distance measuring means 18 are preferably mounted on a suitable support element 24 such as a printed circuit board, or the like.

According to the preferred embodiment, the distance measuring means 18 comprise at least one rotary encoder 26 having an input rotatable shaft 28 and a spring loaded reel 30 coupled thereto, where the spring loaded reel 30 stores one end of a non-stretchable string 32. The number of rotary encoders 18 is determined as a function of a number of adjacent beacon devices which distances shall be measured with respect to a first beacon device.

It is to be understood that, although the input rotatable shaft 28 is shown projecting perpendicularly from the surface of the substantially planar support 24, the input rotatable shaft 28 may as well be projecting in a parallel orientation relative to the support 24, and at an angle relative to the circumferential edge of the latter.

Each rotary encoder 26 disposed on a first edge of a first beacon device 16 is adapted to be in cooperative relation with a corresponding rotary encoder 26 disposed on a facing edge of an adjacent beacon device 16. Thus, as illustrated in FIG. 2, a pair of cooperating rotary encoders 18 located on opposing facing edges of two adjacent beacon devices 16 may share a single string 32 having its ends wrapped around their respective spring loaded reels 30. At least one of the rotary encoders 18 provides rotational measurement values of the rotatable reel 30.

At an initial state, when the body suit 12 is unworn, the input rotatable shafts 28 associated with the rotary encoders 18 are immobile and the strings extending between the cooperating rotary encoders 18 have a first length. When the body suit 12 is worn, at least a part of the body suit 12 stretches as a function of the physical dimensions of the wearer. The effect is that the beacon devices shift position and the distance between the beacon devices 16 located within the stretched part of the body suit 12 increases and the input rotatable shafts 28 associated with the rotary encoders 26 rotate. The string extending between each two adjacent rotary encoders 26 extends and reaches a final length. The rotating amount of each input rotatable shaft 28 is measured and stored inside the storage means 42 of its corresponding beacon device 16. This value allows for determining the final string length. Thus, a pair of rotary encoders 18 allows for accurately measuring the distance between two adjacent beacon devices 16.

It is to be understood that rotary encoders 18 can be replaced by any other suitable distance measuring means that would allow determining a distance between two adjacent beacon devices 16. For instance, the rotary encoders can be replaced by uniquely identified wire loaded reels disposed within the beacon devices in accordance with a reel configuration known a priori, where the wire loaded reels store electrical wires, such that when the beacon devices shift position, the electrical wires unfold and extend in length proportionally to the shifting. Since an electrical property of an electrical wire vary as a function of its length, the distance measuring means can comprise electrical means for measuring electrical properties of the wires when unfolded by effect of the shifting. Such electrical properties can be capacitances or inductances of the wires.

Moreover, it would be possible to use stretchable strings (instead of non-stretchable strings) and to measure the tension of these strings when the beacon devices shift position. Also, it would be also possible to use a proximity sensor technology that would allow measuring the relative distance between two adjacent beacon devices. By using such proximity sensor technology, there is no need to engage a string or any other physical connection between the beacon devices 16.

As shown in FIGS. 2 and 3, a beacon device 16 may have a substantially planar and square shape, and include four rotary encoders 18 equidistantly disposed about the circumference thereof. The beacon device 16 may be encased in any suitable shield case, such as a molded plastic housing or the like, for protection and durability. The shield case may have suitably disposed lateral holes for freely engaging each outwardly extending string 32 of the rotary encoders 18.

It is to be understood that, although the beacon devices 16 illustrated in FIGS. 2 and 3 have a substantially square and planar shape, a beacon device 16 may have any other suitable shape. For example, a beacon device 16 may have a substantially two-dimensional, rounded, triangular, octagonal, or oval shape, or the like, or even a freeform shape. A beacon device 16 may as well have a three-dimensional spherical, triangular, rectangular, or cubic shape, or the like, or even a freeform shape.

As mentioned above, the distance measuring means 18 located within a first beacon device 16 can be adapted to measure the distance between said first beacon device and at least one adjacent beacon device. The strings 32 may extend around the circumference of a two-dimensional beacon device 16, or extend outwardly from the outer surface of a three-dimensional beacon device (not shown). Furthermore, the extending strings 32 need not to be equidistantly distributed around the circumferential edge of a two-dimensional beacon device 16 or about the surface of a three-dimensional beacon device. For example, the extending strings 32 of a plurality of rotary encoders 18 located within a same beacon device 16 may all be outwardly extending from selected positions along a same edge, or along a same surface portion of the device 16.

The apparatus 10 of the present invention may include a combination of beacon devices 16 having a combination of two-dimensional and three-dimensional shapes. It is to be noted that beacon devices 16 having a two-dimensional or a three-dimensional freeform shape may be advantageously used with a body suit 12 having portions adapted to comfortably cover challenging parts of a wearer's body such as the arm pits or ankles of the wearer.

In another embodiment of the present invention, the beacon device 16 may also comprise an accelerometer 36, a timer 38 and a central processing unit (CPU) 40. The accelerometer 36 may consist of a conventional accelerometer that is commonly found in cellular phones, video game devices, or the like, and is configured to measure the relative angular movement in space of the beacon device 16. The timer 38 may consist of a conventional timer and is designed to provide a time stamped value that may be associated with other measurement values obtained by the beacon device 16. The CPU 40 can be connected to the storage means 42 for managing software execution and data storage associated with the beacon device operation. However, for complexity reasons, it would be preferable not to include a CPU within the beacon devices.

It is to be understood that the various elements of the beacon device 16 described herein may be embedded within an integrated circuit (IC) mounted on the support element 24 for obtaining a beacon device 16 having a relatively compact format.

The communication means 44 preferably comprise a data transmitting module connected to the storage means 42, a data communication network and a network interface for transmitting the measurement values (i.e. distance and angular movement values if it is the case) to the central communication unit 20. The data transmitting module can consist of a wireless transmitter or any other appropriate module (wireless or not) for transmitting data to the central communication unit 20. Furthermore, it is be understood that the storage means 42 can consist of a memory or any other electronic component (ex. a multiplexer) configured to receive and store data at least temporally. Thus, the communication network interface unit 44 of each beacon device 16 is connected to the central communication unit 20 through the data communication network. In other terms, the central communication unit 20 is connected, through the data communication network, to each one of the beacon devices for receiving measurement data thereof. Preferably, the central communication unit 20 has a relatively small size, and may be affixed to an edge portion of the body suit as illustrated by FIG. 1.

Figure 4:
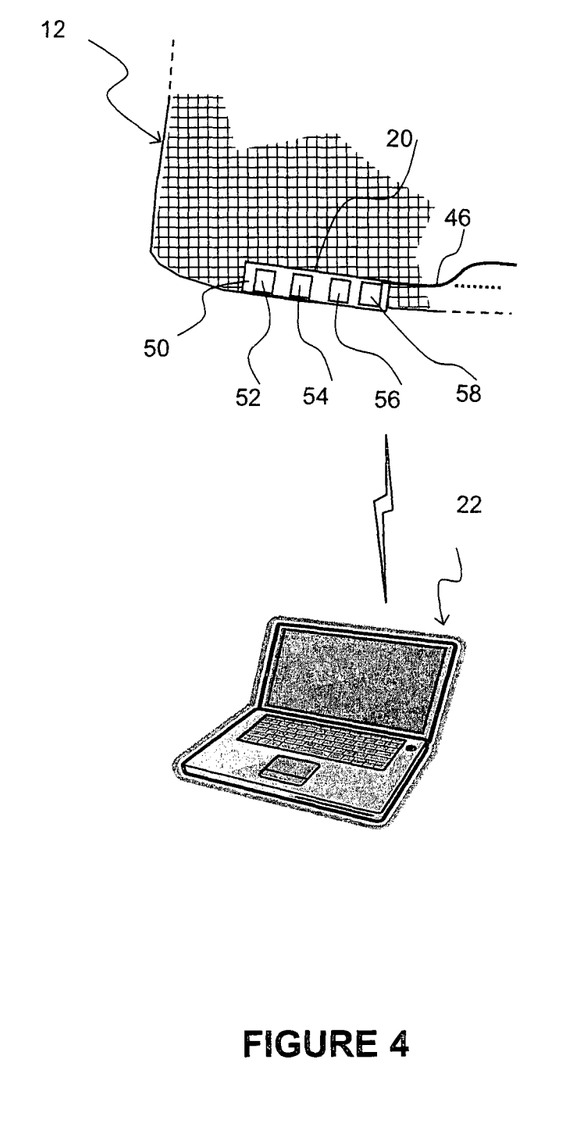
FIG. 4 illustrates a communication connection established between the central communication unit of the apparatus in accordance with the present invention and a remote computer system.
Figure 5:
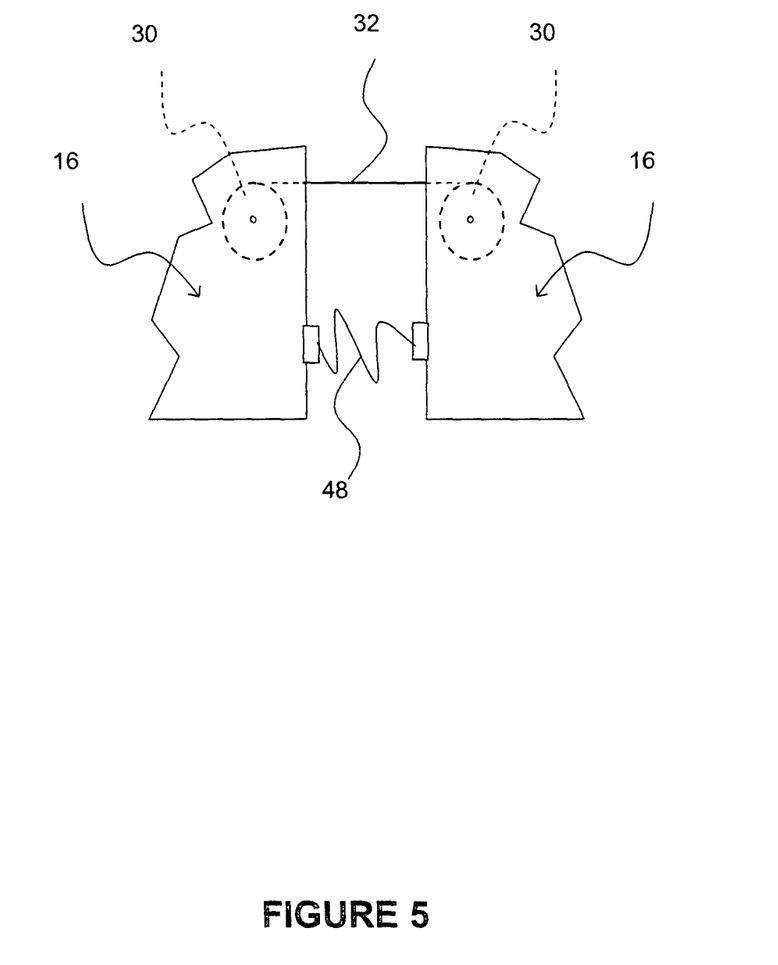
FIG. 5 depicts, in a partial view, a pair of beacon devices connected by a multiconductor wire.

In a preferred embodiment, the data communication network used for communicating data between the central communication unit 20 and the beacon devices 16 is a wire communication network having a daisy-chained configuration. In this optic, as illustrated in FIG. 4, the central communication unit 20 is connected to a first beacon device 16 using a flexible multiconductor wire 46. The wire passes through all the beacon devices, from one beacon device to another in a daisy-chain configuration. As illustrated in FIG. 5, the flexible multiconductor wire between two beacon devices 48 shall have a total length that is at least equivalent to the maximum stretchability between two adjacent beacon devices. It is to be noted that the multiconductor wires may be replaced with a substantially flat and flexible printed circuit conductors (not shown). In another embodiment, the bi-directional data communication network used for communicating data between the central communication unit 20 and the plurality of beacon devices 16 consists of a bi-directional radio-frequency (RF) based communication network. Such a wireless communication network may comprise, for example, a low-power, bi-directional RFID technology (Radio-Frequency interference IDentification technology), or the like.

As illustrated in FIG. 4, the central communication unit 20 is remotely connected via a data network to a remote computer system 22 for transmitting thereto the measurement values received from the beacon devices for further processing. The data network can consist of either a wired or a wireless communication network (such as the Internet or a satellite). The central communication unit 20 comprises a central processing unit (CPU) 52, storage means 54, a network interface 56, and a rechargeable power battery 58.

The network interface 56 is used as an interface for connecting the central communication unit 20 to the beacon devices 16 using the multiconductor wire 46. The communication network interface 56 also serves as a communication interface between the central communication unit 20 and the remote computer system 22. The connection between the communication network interface 56 and the remote computer system 22 may be a wired type connection such as, for example, a conventional USB (Universal Serial Bus) connection, a broadband cable connection, or the like, or may be a wireless type connection such as, for example, a Bluetooth™ or Wi-Fi wireless network connection, or the like. Preferably, the central communication unit 20 communicates with the remote computer system 22 through a wireless connection, such as a Bluetooth™, satellite or Wi-Fi connection.

The electronic measuring apparatus can be used in connection with a plurality of applications, such as e-commerce applications. In the context of e-commerce, the remote computer system 22 can be a mediator server (electronic market database) connected to the Internet and listing clothing items for trade. The mediator server can comprise a web-based application allowing users to select a given clothing item for purchase and to upload measuring values obtained by the electronic measuring apparatus located at the user side. This is particularly useful where the user wishes to order a customized size of an clothing item to purchase, in order to fit with his irregular body size (ex. long legs, broad shoulders, thick neck, etc.).

The rechargeable power battery 58 provides power to the central communication unit 20 as well as to the beacon devices 16 if necessary via the multiconductor wires 48 or independent wires. Preferably, the rechargeable power battery is recharged through the USB connection. Alternatively, the rechargeable battery can also be recharged with an independent power source.

The CPU 52 manages all the operations of the central communication unit 20 for receiving the data from the beacon devices, storing it into the storage means 54 and for transmitting it to the remote computer system 22 through the communication network interface 56. The central communication unit 20 is preferably affixed to a suitable portion of the body suit 12 in a way that does not interfere with the relative movement between the beacon devices 16.

The functionalities of the apparatus 10 may be generally described as follows. As a first step, the body suit 12 is preferably hanging on a cloth hanger, or laid flat on a substantially planar surface, such that the distance measuring means 18 between the beacon devices 16 are in a substantially unstretched state. In a second step, a reset signal is transmitted to each of the beacon devices 16 for resetting to zero each of its onboard distance measuring means 18, its accelerometer unit 36 and its timer unit 38. The reset signal can be initiated by the remote computer system 22, locally using an appropriate reset switch connected to the central communication unit 20 or automatically when the body suit is in a non-stretched state.

In a third step, a wearer (desiring to measure his physical size) wears the body suit 12 in a most natural and comfortable fashion while preferably standing up. During this operation, the beacon devices 16 measure a number of rotations engaged by each spring-loaded reel 30 of each beacon device 16. A first reading is taken at a first moment, such as when a person inhales, and a second reading is taken in a second moment, such as when a person exhales. These values, along with the values, obtained by the accelerometer unit 36 and the timer unit 38 (if it is the case), are stored into the storage means 42 of the corresponding beacon device 16.

In a fourth step, each one of the beacon devices transmit the data stored within its storage means 42 along with a unique identifier associated with the corresponding beacon device 16 to the central communication unit 20 for storage into the storage means thereof 54. This operation can be initiated either automatically or following a request from the central communication unit 20. In a fifth step, the central communication unit 20 transmits the stored data to the remote computer system 22 for further processing. This operation can be initiated either automatically by the central communication unit 20 or upon a request from the remote computer system 22.

Finally, the data (representing the rotational measurement values) may then be processed by the remote computer system for determining the second spatial configuration first, and then for determining the physical dimensions of the wearer by compiling the first and second spatial configurations using an appropriate software. The distances between the beacon devices are already stored in the central communication unit. Each two beacon devices have their distance values assigned to zero after the reset stage (first stage). After the person puts on the cloth or whatsoever, the distances between these beacon devices change and so are the values which are being stored and known already in the central unit. In combination with the accelerometer position the shape of the body that wore the cloth etc can be determined. Each angle of the reel would be noticed in the software as a specific distance (e.g. 1 mm). Each reel of course has a maximum measurement that it can measure. The result of the processed data may then be used to select or custom tailor garments having compatible clothing sizes with the wearer of the measuring apparatus.

Among the advantages of the present measuring apparatus 10 are that it is relatively easy to use by a common person for accurately measuring physical dimensions of a wearer. Also, the apparatus is relatively easy and economical to manufacture and it can be easily folded into a compact format for shipping by regular post mail, thus avoiding a potential customer to travel long distances to try a specific piece of garment at a retail store.

The features disclosed in the foregoing description, in the claims and/or in the accompanying drawings may, both separately and in any combination thereof, be material for realising the invention in diverse forms thereof.

The invention claimed is:

1. A measuring apparatus for determining dimensions of an object, comprising:
   a stretchable material;
   a plurality of uniquely identified beacon devices connected to the stretchable material, the beacon devices comprising:
      a measuring means for measuring spatial configurations between the plurality of beacon devices;
   a processing unit, wherein the processing unit receives the spatial configurations from the plurality of beacon devices thereby determining the dimensions of the object;
   wherein the measuring means comprises a rotary encoder, the rotary encoder including:
      a rotatable shaft;
      a reel coupled to the rotatable shaft; and
      a string, wherein a first end of the string is connected to the reel and a second end is connected to an attachment point on the stretchable material;
   wherein the rotation of the rotatable shaft varies according to a distance between the beacon device and the associated attachment point;
   wherein the processing unit calculates a distance value and an orientation value of the beacon device by measuring the rotation of the rotatable shaft;
   the beacon devices are adjacent; and
   wherein each beacon device includes a number of string loaded wheels equivalent to the number of adjacent beacon devices such that each pair of string loaded reels located within adjacent beacon devices are linked there-between by a common string extending from their respective wheels.

2. The measuring apparatus of claim 1, wherein:
the stretchable material is a garment having a shape adapted to fit a surface of the object; and
the spatial configuration includes:
a first spatial configuration representing a first position of a beacon device; and
a second spatial configuration representing a second position of the beacon device.

3. The measuring apparatus of claim 2, wherein:
the beacon device has a first spatial configuration when the stretchable material is unstretched; and
the beacon device has a second spatial configuration when the stretchable material is stretched.

4. The measuring apparatus of claim 2, wherein the spatial configurations between the plurality of beacon devices includes distance and orientation of each beacon device with respect to the other beacon devices.

5. The measuring apparatus of claim 1, wherein the measuring means comprises a proximity sensor.

6. The measuring apparatus of claim 1, wherein:
the stretchable material further comprises:
a central communications device; and
a communications means connected to the plurality of beacon devices and the central communications unit;
wherein the central communications device:
receives spatial configurations from the beacon devices;
maps the spatial configurations among the beacon devices by which the configurations were generated; and
transmits the mapped spatial configurations to the processing unit.

7. The measuring apparatus of claim 6, wherein:
the beacon devices include a storage means for storing the spatial configuration of the associated beacon device; and
the communications means is connected to the plurality of beacon device storage means.

8. The measuring apparatus of claim 1, wherein the processing unit is a remote processing unit.

9. The measuring apparatus of claim 1, wherein the spatial configurations comprise distance.

10. The measuring apparatus of claim 1, wherein the beacon devices are arranged in an array.

11. A measuring apparatus for determining dimensions of an object, comprising:
a stretchable material;
a plurality of uniquely identified beacon devices connected to the stretchable material, the beacon devices comprising:
a measuring means for measuring spatial configurations between the plurality of beacon devices;
a processing unit, wherein the processing unit receives the spatial configurations from the plurality of beacon devices thereby determining the dimensions of the object;
wherein the measuring means comprises a rotary encoder, the rotary encoder including:
a rotatable shaft;
a reel coupled to the rotatable shaft; and
a string, wherein a first end of the string is connected to the reel and a second end is connected to an attachment point on the stretchable material;
wherein the rotation of the rotatable shaft varies according to a distance between the beacon device and the associated attachment point;
wherein the processing unit calculates a distance value and an orientation value of the beacon device by measuring the rotation of the rotatable shaft; and
wherein the attachment point includes a dump beacon device selected from among the plurality of beacon devices.

12. A measuring apparatus for determining dimensions of an object, comprising:
a stretchable material;
a plurality of uniquely identified beacon devices connected to the stretchable material, the beacon devices comprising:
a measuring means for measuring spatial configurations between the plurality of beacon devices;
a processing unit, wherein the processing unit receives the spatial configurations from the plurality of beacon devices thereby determining the dimensions of the object;
wherein the measuring means comprises stretchable string connected to an attachment point on the stretchable material;
wherein the processing unit calculates a distance value and an orientation value by measuring the tension of the stretchable string; and
wherein the attachment point includes a dump beacon device selected from among the plurality of beacon devices.

13. A measuring apparatus for determining dimensions of an object, comprising:
a stretchable material;
a plurality of uniquely identified beacon devices connected to the stretchable material, the beacon devices comprising:
a measuring means for measuring spatial configurations between the plurality of beacon devices;
a processing unit, wherein the processing unit receives the spatial configurations from the plurality of beacon devices thereby determining the dimensions of the object;
wherein the measuring means comprises a rotary encoder, the rotary encoder including:
a rotatable shaft;
a reel coupled to the rotatable shaft; and
a string, wherein a first end of the string is connected to the reel and a second end is connected to an attachment point on the stretchable material;
wherein the rotation of the rotatable shaft varies according to a distance between the beacon device and the associated attachment point;
wherein the processing unit calculates a distance value and an orientation value of the beacon device by measuring the rotation of the rotatable shaft;
wherein the attachment point includes a dump beacon device selected from among the plurality of beacon devices;
wherein the measuring means comprises a wire loaded reel, the wire loaded wheel including:
a reel;
an electrical wire, wherein a first end of the wire is connected to the reel and a second end of the wire is connected to an attachment point on the stretchable material;

wherein the electrical property of the wire varies according to the length of the wire between the beacon device and the associated attachment point; and the processing unit calculates a distance value and an orientation value by measuring the electrical property of the wire.

14. The measuring apparatus of claim 13, wherein the electrical properties include electrical resistance of the wire.

15. The measuring apparatus of claim 14, further comprising:
a central communications device;
a communications means connected to the plurality of beacon devices and the central communications unit;
wherein the central communications device:
receives the electrical properties from the beacon devices;
maps the spatial configurations among the beacon devices by which the configurations were generated; and
transmits the mapped spatial configurations to the processing unit.

16. The measuring apparatus of claim 13, wherein:
the beacon devices are adjacent; and
each beacon device includes two or more rotary encoders wherein the reel of each rotary encoder on a beacon device is connected by a wire to the reel of a rotary encoder on an adjacent beacon device.

17. A measuring apparatus for determining a dimension of an object, comprising:
a stretchable material;
at least one attachment point connected to the stretchable material;
a plurality of uniquely identified beacon devices connected to the stretchable material, the beacon device comprising:
a rotary encoder, comprising:
a rotatable shaft;
a spring loaded reel coupled to the rotatable shaft; and
a string, wherein a first end of the string is connected to the reel and at least one attachment point;
wherein the beacon device has a first spatial configuration when the stretchable material is unstretched representing a first position of the beacon device;
wherein the beacon device has a second spatial configuration when the stretchable material is stretched representing a second position of the beacon device;
wherein the rotation of the rotatable shaft varies according to a distance between the beacon device and an associated attachment point; and
a processing unit, wherein the processing unit receives the first and second spatial configurations from the plurality of beacon devices and calculates a distance value of the beacon device by measuring the rotation of the rotatable shaft.

18. The measuring apparatus of claim 17, wherein:
each rotary encoder is disposed on a first edge of a first beacon device; and
the at least one attachment point is an adjacent rotary encoder.

19. The measuring apparatus of claim 17, further comprising:
an encoder connected to each beacon device configured to measure the angular movement of the associated beacon device;
a timer connected to each beacon device configured to provide a time stamp value associated with the first and second spatial configurations.

20. The measuring apparatus of claim 17, further comprising:
a central communications unit connected to the stretchable material; and
a bi-directional communications network interconnecting the plurality of beacon devices with the central communications unit.

21. The measuring apparatus of claim 20, wherein the bi-directional communications network is a flexible electrical conductor.

22. The measuring apparatus of claim 17, wherein the processing unit is located at a remote computer system.

23. The measuring apparatus of claim 22, wherein the dimensions of the object are used to manufacture clothing.

24. A measuring apparatus for determining dimensions of an object, comprising:
a garment having a shape adapted to fit a surface of an object, wherein when in contact with the object the garment stretches in proportion to the surface;
a plurality of uniquely identified beacon devices disposed on the garment;
wherein, when the garment is in a first unstretched spatial configuration known a prioi when the garment is not in contact with the object;
wherein, when the garment is stretched when in contact with the object, the beacon devices shift from a first unstretched spatial configuration to a second spatial configuration conforming to the surface;
an electronic means, for detecting the second spatial configuration, wherein the electronic means generates data representing the second spatial configuration;
a processing unit, the processing unit configured to receive data associated with the first and second spatial configurations for calculating the dimension of the surface;
wherein the electronic means comprises distance measuring means;
wherein the distance measuring means allows for determining a shifting length and a shifting orientation of each one of the beacon devices when the beacon devices shift position;
wherein the distance measuring means comprises uniquely identified rotary encoders disposed within at least a part of the uniquely identified beacon devices in accordance with a rotary encoder configuration known as a priori;
wherein the rotary encoders comprise input rotatable shafts coupled to spring loaded reels storing strings; and
wherein the strings have a first end folded within the spring loaded reels and a second end extending therefrom and attached to attachments points located at selected directions in accordance with the rotary encoder configuration, such that when the beacon devices shift position, the strings unfold and engage the input rotatable shafts to rotate proportionally to the shifting.

25. The measuring apparatus of claim 24, wherein each one of the beacon devices comprises a number of rotary encoders equivalent to the number of adjacent beacon devices such that each pair of rotary encoders located within adjacent beacon devices are linked therebetween by a common string extending from their respective spring loaded reels.

26. The measuring apparatus of claim 24, wherein the attachment points consist of dump beacon devices selected from among the beacon devices.

27. The measuring apparatus as claimed in claim 24, wherein:
the strings are non-stretchable strings;
the rotary encoders are configured to output rotational values proportional to the shifting when the input rotatable shafts rotate; and
the shifting length and shifting orientation of each one of the beacon devices is determined as a function of the rotary encoder configuration and the rotational values.

28. The measuring apparatus of claim 27, wherein:
the beacon devices comprise storage means for storing the rotational values; and
wherein the communications means are connected to the storage means for retrieving the rotational values.

29. The measuring apparatus of claim 27, further comprising:
a central communications unit;
a communications means connected to the beacon devices and to the central communications unit;
wherein the central communications unit:
receives the rotational values from the beacon devices;
maps each rotational value among the rotational values with a corresponding rotary encoder among the rotary encoders with which it was generated; and
remotely transmits the mapped rotational values to the processing unit.

30. The measuring apparatus of claim 29, wherein:
the processing unit is part of a remote computer system; and
the central communications unit further comprises:
a network interface adapted to be connected to a data network for remotely transmitting the mapped rotational values to the processing unit.

31. A measuring apparatus for determining dimensions of an object, comprising:
a garment having a shape adapted to fit a surface of an object, wherein when in contact with the object the garment stretches in proportion to the surface;
a plurality of uniquely identified beacon devices disposed on the garment;
wherein, when the garment is in a first unstretched spatial configuration known a prioi when the garment is not in contact with the object;
wherein, when the garment is stretched when in contact with the object, the beacon devices shift from a first unstretched spatial configuration to a second spatial configuration conforming to the surface;
an electronic means, for detecting the second spatial configuration, wherein the electronic means generates data representing the second spatial configuration;
a processing unit, the processing unit configured to received data associated with the first and second spatial configurations for calculating the dimension of the surface;
wherein the electronic means comprises distance measuring means;
wherein the distance measuring means, further comprise:
uniquely identified wire loaded reels disposed within at least a part of the uniquely identified beacon devices in accordance with a reel configuration know a priori; and
wherein the wire loaded reels sore electrical wires having a first end folded within the wire loaded reels and a second end extending therefrom and attached to attachment points located at selected directions in accordance with the reel configuration, such that when the beacon devices shift positions, the electrical wires unfold and extend in length proportionally to the shifting.

32. The measuring apparatus of claim 31, wherein the attachment points consist of dump beacon devices selected from among the beacon devices.

33. The measuring apparatus of claim 31, wherein:
the distance measuring means further comprises electrical means for measuring electrical properties of the wires when unfolded by the shifting, the electrical properties varying as a function of the length of the wires; and
the shifting length and shifting orientation of each one of the beacon devices is determined as a function of the reel configuration and the measured electrical properties.

34. The measuring apparatus of claim 33, wherein the electrical properties consist of electrical resistances or conductances of the wires.

35. The measuring apparatus of claim 34, further comprising:
a central communications unit;
a communications means connected to the beacon devices and to the central communications unit;
wherein the central communications unit:
receives the measured electrical properties from the beacon devices;
maps each measured electrical property among the measured electrical properties with a corresponding wire reel among the wire reels associated therewith; and
remotely transmits the mapped measured electrical properties to the processing unit.

36. The measuring apparatus of claim 35, wherein:
the processing unit is part of a remote computer system;
the central communications unit further comprises:
a network interface adapted to be connected to a data network for remotely transmitting the mapped measured electrical properties to the processing unit.

37. The measuring apparatus of claim 35, wherein:
the beacon devices comprise storage means for storing the measured electrical properties; and
wherein the communications means are connected to the storage means for retrieving the measured electrical properties.

38. The measuring apparatus of claim 37, wherein the beacon devices are disposed on the garment in a two dimensional array configuration wherein each beacon device has a number of adjacent beacon devices located at different directions thereof.

* * * * *